(12) United States Patent  
Long et al.

(10) Patent No.: US 8,961,776 B2  
(45) Date of Patent: Feb. 24, 2015

(54) MOLECULAR METAL-OXO CATALYSTS FOR GENERATING HYDROGEN FROM WATER

(75) Inventors: Jeffrey R. Long, Oakland, CA (US); Christopher J. Chang, Berkeley, CA (US); Hemamala I. Karunadasa, Palo Alto, CA (US)

(73) Assignee: The Regents of the University of California, Oakland, CA (US)

(*) Notice: Subject to any disclaimer, the term of this patent is extended or adjusted under 35 U.S.C. 154(b) by 332 days.

(21) Appl. No.: 13/499,886

(22) PCT Filed: Sep. 10, 2010

(86) PCT No.: PCT/US2010/048405  
§ 371 (c)(1),  
(2), (4) Date: May 9, 2012

(87) PCT Pub. No.: WO2011/043893  
PCT Pub. Date: Apr. 14, 2011

(65) Prior Publication Data  
US 2012/0228152 A1    Sep. 13, 2012

Related U.S. Application Data

(60) Provisional application No. 61/249,877, filed on Oct. 8, 2009.

(51) Int. Cl.
| | |
|---|---|
| C07F 15/02 | (2006.01) |
| C07F 1/08 | (2006.01) |
| C25B 1/04 | (2006.01) |
| C07F 7/28 | (2006.01) |
| C07F 13/00 | (2006.01) |
| C07F 9/00 | (2006.01) |
| C07F 15/06 | (2006.01) |
| C07F 11/00 | (2006.01) |

(52) U.S. Cl.  
CPC .................................. *C07F 11/005* (2013.01)  
USPC ............................................. 205/637; 546/2

(58) Field of Classification Search  
None  
See application file for complete search history.

(56) References Cited

U.S. PATENT DOCUMENTS

2003/0105306 A1* 6/2003 Grubbs et al. ............... 536/1.11

OTHER PUBLICATIONS

Takacs, Synthesis and Characterization of New do Tungsten and Molybdenum Imido Complexes with Heteroatomic Bifunctional O—N Chelate Ligands, Inorg. Chem 33, 2635-2638 (1994).*  
International Searching Authority, Written Opinion on PCT/US10/48405 (2011).*

* cited by examiner

*Primary Examiner* — Yun Qian  
(74) *Attorney, Agent, or Firm* — Lawrence Berkeley National Laboratory (57) ABSTRACT

A composition of matter suitable for the generation of hydrogen from water is described, the positively charged cation of the composition having the general formula $[(PY5W_2)MO]^{2+}$, wherein $PY5W_2$ is $(NC_5XYZ)(NC_5H_4)_4C_2W_2$, M is a transition metal, and W, X, Y, and Z can be H, R, a halide, $CF_3$, or $SiR_3$, where R can be an alkyl or aryl group. The two accompanying counter anions, in one embodiment, can be selected from the following $Cl^-$, $I^-$, $PF_6^-$, and $CF_3SO_3^-$. In embodiments of the invention, water, such as tap water containing electrolyte or straight sea water can be subject to an electric potential of between 1.0 V and 1.4 V relative to the standard hydrogen electrode, which at pH 7 corresponds to an overpotential of 0.6 to 1.0 V, with the result being, among other things, the generation of hydrogen with an optimal turnover frequency of ca. 1.5 million mol $H_2$/mol catalyst per h.

2 Claims, 6 Drawing Sheets

FIG. 1

Electrocatalytic cycle for the reduction of water to release hydrogen and hydroxide anions.

MOLECULAR METAL-OXO CATALYSTS FOR GENERATING HYDROGEN FROM WATER

CROSS REFERENCE TO RELATED APPLICATIONS

This application claims priority to PCT Application PCT/US2010/048405, filed Sep. 10, 2010, which in turn claims priority to U.S. Provisional Patent Application Ser. No. 61/249,877, filed Oct. 8, 2009, entitled Molecular Metal-Oxo Catalysts for Generating Hydrogen from Water, the entire contents of which application is incorporated herein by reference as if fully set out herein in its entirety.

STATEMENT OF GOVERNMENTAL SUPPORT

The invention described and claimed herein was made in part utilizing funds supplied by the U.S. Department of Energy under Contract No. DE-AC02-05CH11231 and the National Science Foundation under Contract No. CHE-0617063. The government has certain rights in this invention.

BACKGROUND OF THE INVENTION

1. Field of the Invention

This invention relates generally to a new composition of matter and, more specifically, to a new high oxidation state metal-oxo catalyst which can be used for generating hydrogen from water, in one embodiment the high oxidation state metal being molybdenum.

2. Brief Description of the Related Art

Owing to issues of climate change and accelerating global energy demands, the search for viable carbon-neutral sources of renewable energy is amongst the foremost challenges in science today. One such alternative is hydrogen, which can potentially be used as a clean replacement for fossil fuels in many applications, including transportation in cars, buses, trucks, trains, and airplanes. It can further be used in fuel cells for powering mobile devices such as lap-top computers and cell phones, as well as for meeting power requirements in buildings and industry. Many industries also use hydrogen as a reactant. One example is the Haber-Bosch process that produces ammonia, which currently relies on steam reforming of natural gas or liquefied petroleum for the production of hydrogen. This is expensive, environmentally unsustainable (based on finite resources of fossil fuel and produces carbon dioxide and hydrogen sulfide, two major atmospheric pollutants) and necessitates removal of sulfur which deactivates the catalyst used for ammonia production. Hydrogen is also used as a reducing agent for metal ores, for the production of hydrochloric acid and as a hydrogenating agent for unsaturated fats and oils.

In this context, where hydrogen has emerged as an attractive candidate for a clean, sustainable fuel as well as a precursor to many essential compounds, an intense interest in creating artificial systems that utilize earth-abundant catalysts for efficient hydrogen production from water has developed. A major quest of this renewable energy research is the search for efficient catalysts for the production of hydrogen from water, which rely on cheap, earth-abundant elements.

Hydrogenase enzymes possessing earth-abundant iron and/or nickel cofactors have been found to catalytically evolve $H_2$ from neutral aqueous solution at its thermodynamic potential, with turnover frequencies of 100-10,000 mol $H_2$/mol catalyst per second. However, the large size and relative instability of these enzymes under aerobic, ambient conditions has led to the search for well-defined molecular complexes outside the biological milieu that can produce $H_2$ from water. Although many examples of air- and moisture-sensitive synthetic iron-sulfur clusters have provided insight into hydrogenase structure and reactivity, they catalyze proton reduction from acids in organic solvents at fairly negative potentials of −0.9 to −1.8 V vs. SHE (the Standard Hydrogen Electrode). Metal complexes that evolve $H_2$ at more positive potentials still require organic acids, additives, and/or solvents. As such, the creation of earth-abundant molecular systems that produce $H_2$ from water with high catalytic activity and stability remains a significant basic scientific challenge.

BRIEF SUMMARY OF THE INVENTION

According to one aspect of this invention a new chemical has been synthesized which achieves the goal of $H_2$ generation through the discovery of a well-defined organo metal-oxo complex that catalytically generates hydrogen from water at neutral pH. In one embodiment, the organo metal-oxo complex is an organo molybdenum-oxo complex, which has been successfully used to generate hydrogen for at least 3 days, with a turnover frequency of 1.47 million mol $H_2$/mol catalyst per hour and a turnover number of 105 million mol $H_2$/mol catalyst. Moreover, this same molecular system was used to evolve $H_2$ from seawater, the earth's most abundant source of protons. Thus, demonstrated herein is that a high-valent metal-oxo unit can be exploited to create reduction catalysts that are robust and functional in water, an approach that has broad implications for the design of green and sustainable chemistry cycles.

The rates of hydrogen production using the organo metal-oxo catalysts are at least one to two orders of magnitude higher than other known molecular electro-catalysts that operate in organic/acidic media. In addition the catalysts of this invention are significantly cheaper than other solid state catalysts currently in use. In the case of molybdenum, for example, its cost is about 74 times lower than the cost of platinum, the current preferred catalyst for hydrogen production. Unlike solid-state catalysts such as platinum metal, the molecular catalyst of the type described has the further advantage that it is also amenable to structural tuning through ligand modification and metal substitution, which may further improve production efficiencies.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

The preferred embodiments are illustrated in the context of the use of a molybdenum-oxo catalyst for the generation of hydrogen. The skilled artisan will readily appreciate, however, that the materials and methods disclosed herein will have application to a number of variants of this composition.

It has been discovered that a certain class of molecules can be particularly useful as catalysts for the generation of hydrogen gas from water. More particularly, these molecules are salts wherein the positive moiety comprises a PY5 metal-oxo ion, and even more particularly where the metal of the PY5 metal-oxo ion is molybdenum. (As used herein, PY stands for pyridine and PY5 indicates the presence of five pyridyl rings). The positively charged cations of the compositions of matter of this invention are described by the general formula [(PY5W$_2$)MO]$^{2+}$, wherein PY5W$_2$ is (NC$_5$XYZ)(NC$_5$H$_4$)$_4$C$_2$W$_2$, M is a high oxidation state metal, and W, X, Y, and Z are selected from the group comprising H, R, a halide, CF$_3$, or SiR$_3$, where R is an alkyl or aryl group. The two accompanying negative ions (i.e. the counter anion) of the metal-oxo salt composition may be selected from any number of anions, including a halide such as Cl$^-$, I$^-$, or PF$_6^-$, CF$_3$SO$_3^-$, and so forth. The exact composition of the negative moiety is not significant as the anion does not play a significant role in the water to hydrogen reaction.

Figure 1:
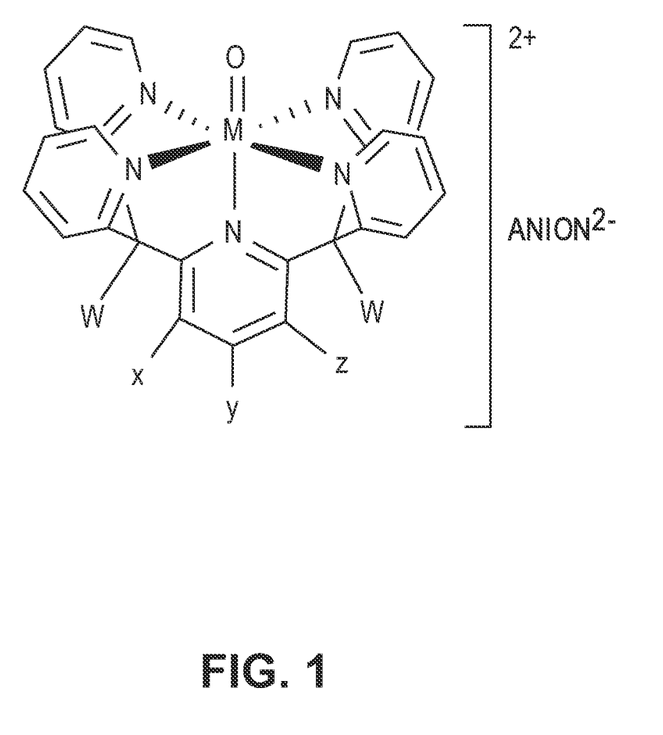
FIG. 1 is a generic, structural formula for the organo metal-oxo complex according to an embodiment of this invention.

A three dimensional model of the high oxidation state metal-oxo ion of the composition of this invention is shown in FIG. 1. Therein, central to the molecule is a metal atom, which in the illustrated embodiment is molybdenum (Mo). The metal can also be one of the following transition metals of the periodic table, including Ti, V, Cr, Mn, Fe, Co, Ni, Cu, and Tungsten. Directly bound to the metal atom is a single oxygen atom, as well as the five pyridyl rings. For the base (or axial) pyridyl ring, the hydrogen atoms at the, X, Y, and Z positions may be substituted with a halogen such as F, Cl, Br, and I or a group such as R, CF$_3$ or SiR$_3$ where R=alkyl or aryl group. Furthermore, the substitutions at the X, Y and Z position may be the same or different. Finally, the group attached to the quaternary carbon at the position may be either hydrogen, methyl, a higher alkyl, or aryl group or any one of the halogen, CF$_3$ or SiR$_3$ groups listed above. These pentapyridine ligand complexes are semi rigid, and in their salt form easily dissolve in water.

It has been found that when placed in water, the molybdenum-oxo salt goes into solution to form the moiety [(PY5Me$_2$)MoO]$^{2+}$. The hydrogen forming reaction in one embodiment is electrolysis driven. Herein, to initiate the hydrogen forming reaction, a negative potential is applied to one of two electrodes positioned within the water bath containing an electrolyte such as sodium phosphate or potassium chloride. In an embodiment, the negative voltage is in the order of 1.0 V to 1.4 V versus the standard hydrogen electrode which at pH 7 corresponds to an overpotential of between 0.6 V to 1.0 V. [As used herein, Overpotential=(applied potential–E(pH 7)), where at pH 7E=–0.4 V.] Upon application of the voltage, the positive metal-oxo moiety migrates to the negative electrode where it picks up electrons. While not intending to be bound by any particular theory regarding the reaction sequence, it is speculated that the catalytic cycle depicted in FIG. 2 is representative of the sequence of steps that results in the conversion of water to hydrogen.

Figure 2:
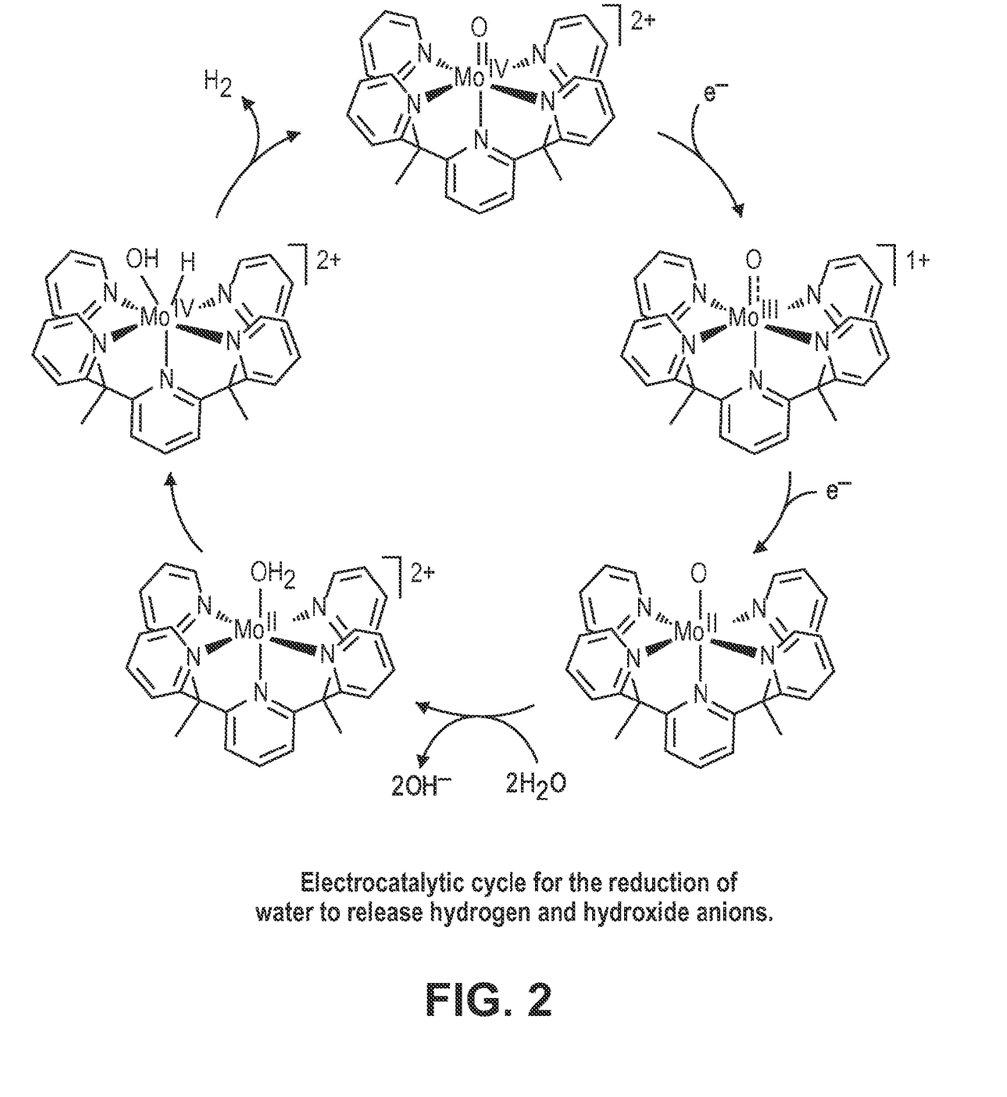
FIG. 2 is a representative depiction of a possible reaction sequence whereby hydrogen gas is evolved by the reaction of water and a molybdenum-oxo complex according to an embodiment of the invention.

More particularly, the catalytic cycle of FIG. 2 depicts a possible pathway for the generation of hydrogen from water mediated by [(PY5Me$_2$)MoO](PF$_6$)$_2$. One-electron reduction of [(PY5Me$_2$MoO]$^{2+}$ gives [(PY5Me$_2$)MoO]$^{1+}$, with the addition of a second electron providing a putative [(PY5Me$_2$)MoO] species. This reduction weakens the Mo—O bond and enhances its nucleophilicity, enabling it to deprotonate nearby water molecules to afford the reactive intermediate [(PY5Me$_2$)Mo(H$_2$O)]$^{2+}$ and release two OH$^-$ anions. The reduced aquo complex in the present scheme then eliminates H$_2$ to regenerate [(PY5Me$_2$)MoO]$^{2+}$.

Observations are consistent with the foregoing Mo$^{II}$/Mo$^{IV}$ cycle. Under reductive catalytic conditions, controlled potential electrolysis (CPE) of solutions of green catalyst [(PY5Me$_2$)MoO](PF$_6$)$_2$ initially turn dark yellow and within about 10 minutes change to a purple-brown color that is maintained for the remainder of the electrolysis. Once the potential is switched off, the solution quickly changes back to the dark yellow color. Chemical reduction of [(PY5Me$_2$)MoO]$^{2+}$ using one equivalent of sodium naphthalenide results in a similar dark yellow solution displaying absorption bands at 226, 264, 452, 473, and 737 nm. These data, together with the reversibility of the first reduction wave in the cyclic voltammogram of [(PY5Me$_2$)MoO](PF$_6$)$_2$ in water, suggest that the dark yellow complex is [(PY5Me$_2$)MoO]$^{1+}$. Reaction of [(PY5Me$_2$)MoO](PF$_6$)$_2$ with two equivalent of sodium naphthalenide further affords a solution with a purple-brown color matching that observed after extended electrolysis. Moreover, upon exposure to air, electrolyzed solutions regenerate green [(PY5Me$_2$)MoO]$^{2+}$, as verified by electronic (UV-visible range radiation) and vibrational (infrared radiation) spectroscopy. It is therefore believed that a PY5Me$_2$ complex of Mo$^{II}$ is responsible for the reductive cleavage of water to release H$_2$ and OH$^-$ ions.

Figure 3A:
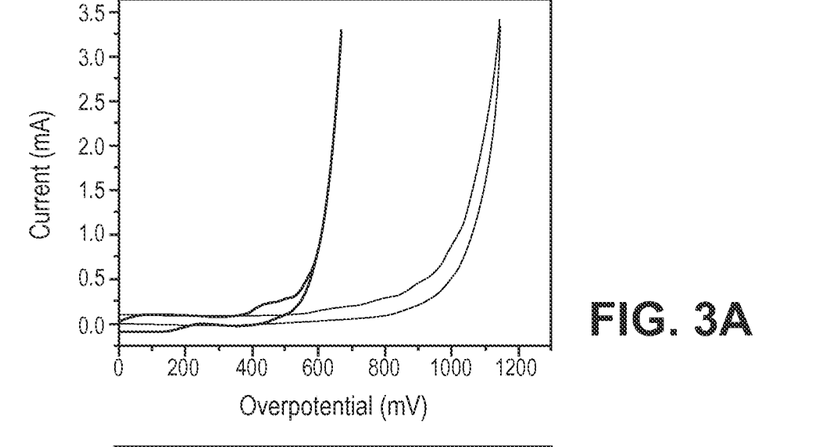
FIG. 3 is a series of graphs depicting electrochemical data obtained for a 7.7 μM solution of $[(PY5Me_2)MoO](PF_6)_2$ in a 0.6 M phosphate buffer at pH 7.
Figure 3B:
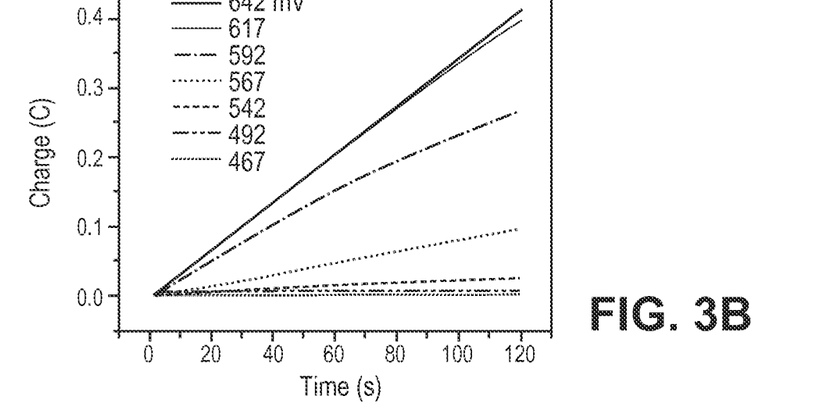
Figure 3C:
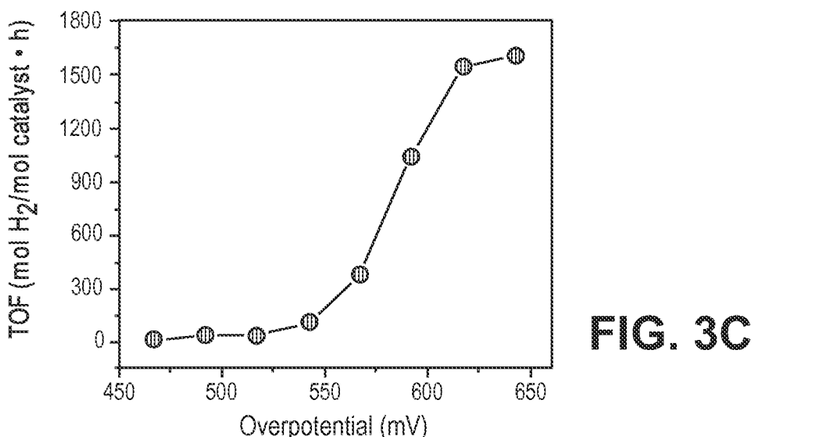

A series of experiments were carried out for one member of the catalysts of this invention, the species of the embodiment being [(PY5Me$_2$)MoO](PF$_6$)$_2$. The particular reaction was carried out in deionized water. The results are illustrated in FIG. 3. More specifically, the data reported in FIG. 3 are electrochemical data for a 7.7 μM solution of [(PY5Me$_2$)MoO](PF$_6$)$_2$ in a 0.6 M phosphate buffer at pH 7. The cyclic voltammograms are for a solution with (the dark line), and without (the light line) the catalyst at a scan rate of 50 mV/s. Plot B graphically depicts the data for charge buildup versus time at various overpotentials. Plot C shows turnover frequency (TOF) versus overpotential. The background solvent activity was subtracted from plots 3B and 3C [Overpotential=applied potential–E(pH7)].

Controlled potential electrolysis (CPE) experiments were carried out in a double-compartment cell to assess the efficacy of the [(PY5Me$_2$)MoO](PF$_6$)$_2$ catalyst. As shown in FIG. 3B, the amount of charge utilized in 2 min increases with increasing overpotential until a saturation value of 0.43 C is reached at 0.64 V. This saturation behavior is due to the potential drop between the working and auxiliary electrodes exceeding the compliance voltage of the potentiostat at high current densities, and is not an inherent property of the catalyst. Assuming that every electron is used for the reduction of protons, and that all the catalyst molecules in solution were producing hydrogen, the TOF for the catalyst was also calculated. The TOF increases with overpotential, reaching a maximum of 1600 mol H$_2$/mol catalyst per hour (FIG. 3C). Control experiments performed using Na$_2$MoO$_4$ or PY5Me$_2$ showed no catalytic activity, and no catalytic activity was observed when fresh electrolyte was added to a used mercury electrode. Moreover, no solid deposits were observed on the mercury electrode, which remained shiny even after extended and repeated electrolysis experiments.

To optimize catalytic TOP and assess the tong-term stability of [(PY5Me$_2$)MoO](PF$_6$)$_2$ as a catalyst, extended CPE experiments were performed using a frit of greater diameter and a higher concentration of electrolyte (3 M phosphate, pH 7) to minimize internal resistance. Remarkably, the catalyst maintained activity under these conditions for at least 71 h, when the measurement was stopped because the concentration of hydroxide ions in the working electrode compartment overcame the capacity of the buffer. Thus, the [(PY5Me$_2$)MoO](PF$_6$)$_2$ catalyst is effective for long durations at close to neutral pH, with its durability apparently limited only by the strength of the buffer. The data obtained in the experiments are reported at FIG. 4, which depicts extended electrolysis data for a 2 μM solution of [(PY5Me$_2$)MoO](PF$_6$)$_2$ in a 3 M pH 7 phosphate buffer, showing charge build-up and turnover number (TON) versus time (open circles), as well as data for the buffer solution alone (the solid line) with the cell operating at a potential of −1.40 V vs. SHE.

Figure 4:
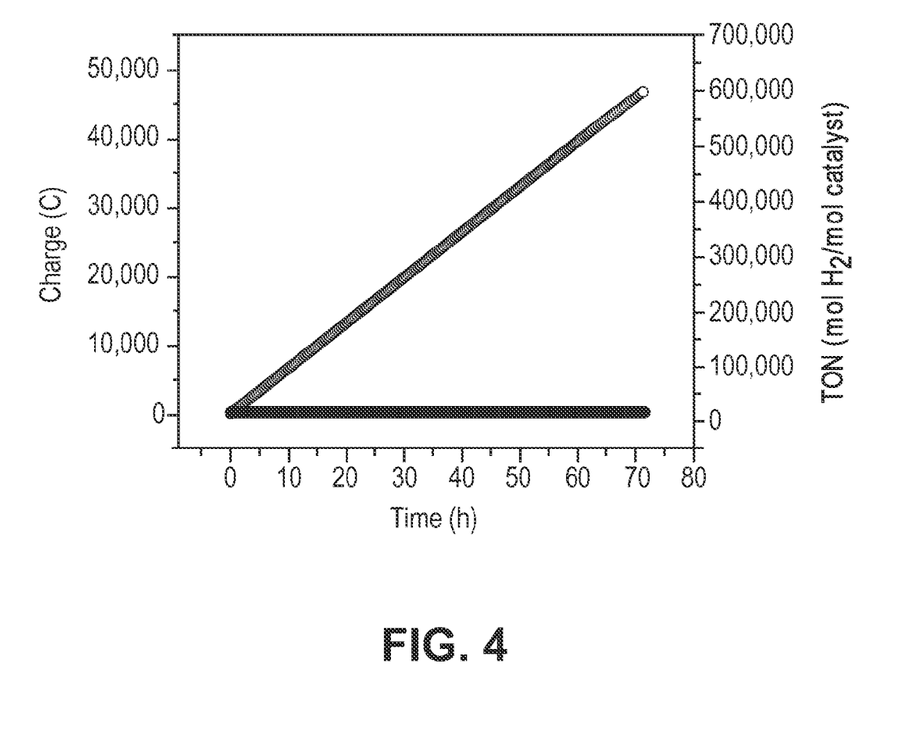
FIG. 4 is a plot of extended electrolysis data for a 2 μM solution of $[(PY5Me_2)MoO](PF_6)_2$ in a 3 M pH 7 phosphate buffer.

In this experiment, the current leveled out at 179 mA, whereas a control experiment run under identical conditions, hut without the catalyst, showed a current of just 1.1 mA. The charge accumulated over this period, after subtracting the contribution from the blank solution, resulted in a TON of 606,000 mol H$_2$/mol catalyst with a TOF of 8510 mol H$_2$/mol catalyst per hour (FIG. 4). It is believed these values are significantly higher than those for other reported molecular catalysts for electrochemical hydrogen production from neutral water, including di-nickel and mono cobalt complexes with TONs of just 100 and 5 mol H$_2$/mol catalyst, respectively. Moreover, the activity of [(PY5Me$_2$)MoO](PF$_6$)$_2$ is comparable to hydrogenase enzymes on a per volume basis, (packing together the number of catalyst molecules needed to fill the volume of a single hydrogenase protein yields hydrogen production rates of 1000-3400 H$_2$ molecules/s) with far greater stability for the former.

Figure 5A:
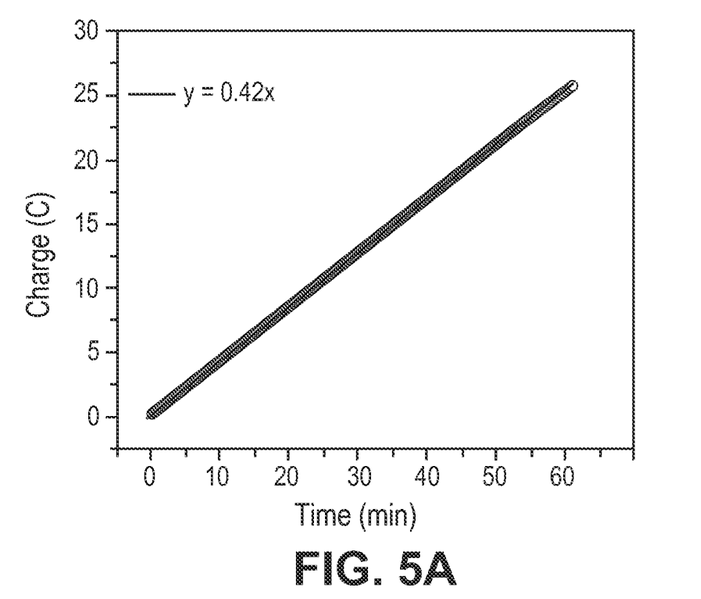
FIG. 5 is a plot of electrochemical data obtained for a 4.2 μM solution of $[(PY5Me_2)MoO](PF_6)_2$ in 1 M KCl.
Figure 5B:
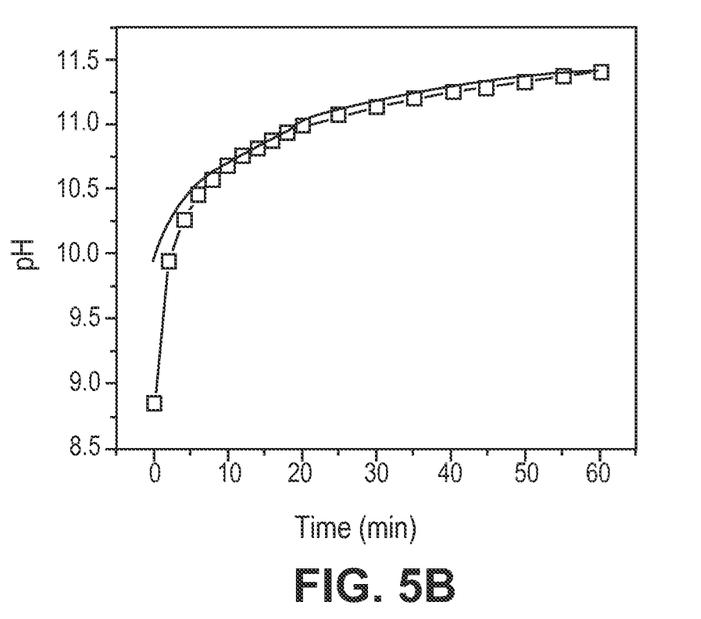

To test the stability of [(PY5Me$_2$)MoO](PF$_6$)$_2$ in the absence of a buffer, CPE experiments were performed in a 1 M aq. KCl solution. Here, accumulation of hydroxide anions as H$_2$ is generated, leads to an increase in pH. The accumulated charge within a given time period can be used to calculate the amount of H$_2$ produced, and, therefore, the concentration of OH$^-$ ions in solution. FIG. 5A plots charge build-up over time at an applied potential of −1.40 V vs. SHE. The linear fit of the data (where the charge vs. time slope {y=0.42x}) evidences current is constant during the measurement (i.e. the catalytic activity is constant, with no decomposition occurring). FIG. 5B, plots the measured change in solution pH with time during electrolysis (squares) and the calculated change in pH assuming the catalyst performs at Faradaic efficiency (continuous line) is plotted. Notably, the agreement between calculated and observed pH changes during a 60-min electrolysis, establishes that the catalyst indeed operates at Faradaic efficiency. Mass spectrometry studies indicate a reduced stability for [(PY5Me$_2$)MoO]$^{2+}$ at high pH, with a significant dissociation of the molybdenum center from the PY5Me$_2$ ligand occurring above pH 12.

Figure 6A:
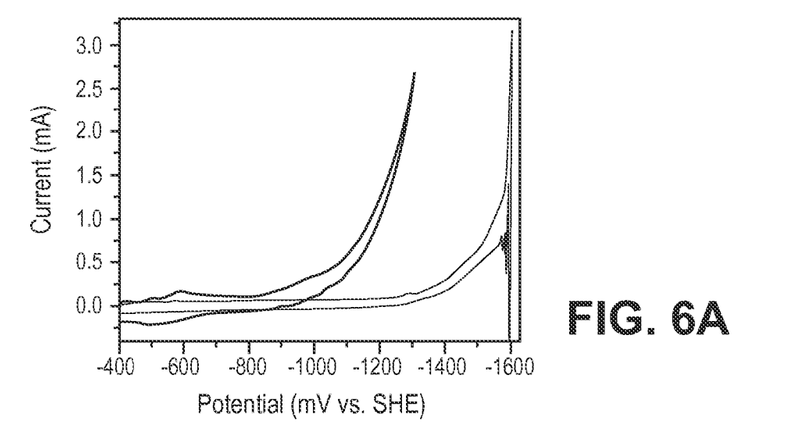
FIG. 6 is a series of graphs similar to those illustrated in FIG. 3 for a 7.7 μM solution of [(PY5Me$_2$)MoO](PF$_6$)$_2$ in sea water.
Figure 6B:
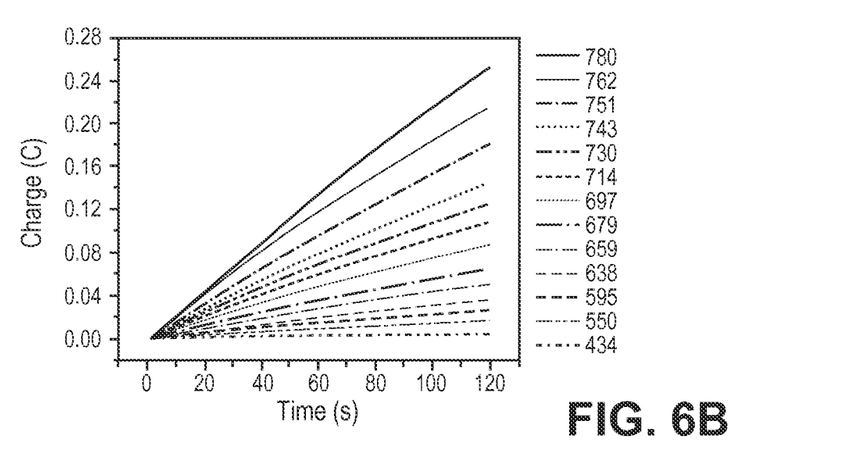
Figure 6C:
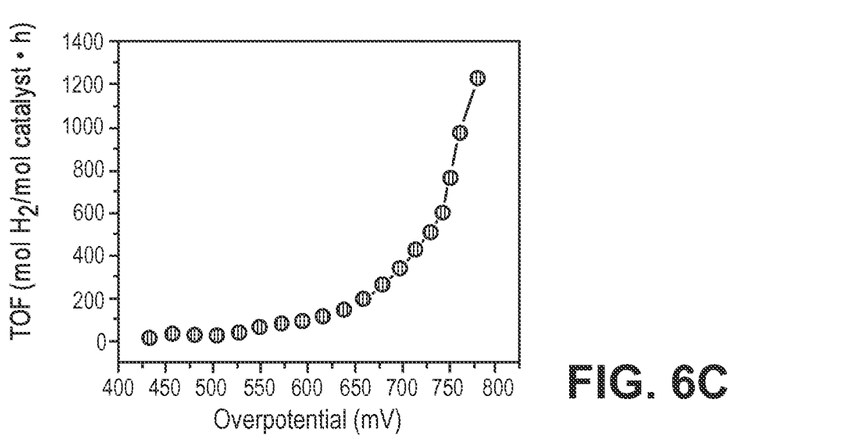

With data showing that the catalyst can tolerate impurities and still show activity in water, performance was evaluated in seawater, the earth's most abundant proton source (FIG. 6). Upon adding [(PY5Me$_2$)MoO](PF$_6$)$_2$ to a sample of California seawater with no added electrolyte, the onset of catalytic current was observed at ea, −0.81 V vs. SHE. In the absence of [(PY5Me$_2$)MoO](PF$_6$)$_2$, a catalytic current was not apparent until a potential of −1.60 V was attained. To obtain an accurate blank subtraction for controlled potential electrolysis (CPE), the charge generated from seawater atone was subtracted from the charge generated from the catalyst solution at the same overpotential, as determined from the solution pH at the end of the electrolysis. CPE experiments performed for short durations in seawater were remarkably similar to the results obtained in pH 7 buffered water. The current saturated at 0.32 C at an applied potential of −1.40 V vs. SHE, corresponding to a turnover frequency of 1225 mol H$_2$/mol catalyst per hour at an overpotential of 0.78 V. The background solvent activity was subtracted from plots 6B and 6C [Overpotential=applied potential−E(pH at the end of the electrolysis)].

An exemplary synthesis route for the obtaining of [(PY5Me$_2$)MoO](PF$_6$)$_2$ is set forth in the following paragraphs. All chemical synthese were conducted under strictly air and moisture-free conditions using standard glove-box and Schlenk-line techniques, unless otherwise noted. The compound MoI$_2$(CO)$_3$(MeCN)$_2$ was synthesized as described in Baker, P. K., Fraser, S. G. Keys, E. M., "The synthesis and spectral properties of some highly reactive new seven-coordinate molybdenum (II) and tungsten (II) bisacetonitrile dihalogenotricarbonyl complexes", J. Organomet. Chem. 309, 319-321 (1986). The compound PY5Me$_2$, was synthesized as described in Canty, A. J., Minchin, N. J., Skelton, B. & White, A. H., "Interaction of Palladium (II) Acetate with Substituted Pyridines, Including a Cyclometalation Reaction and the Structure of [Pd{meso-[(py)PhMeC]$_2$—O$_5$H$_3$N}(O$_2$CMe)][O$_2$CMe]3H$_2$O", J. Chem. Soc., Dalton Trans. 10, 2205-2210 (1986). All other reagents were purchased from commercial vendors and used without further purification. Electronic grade Hg (99.9998%), and platinum gauze were purchased from Alfa Aesar for the electrochemical studies. Toluene, acetonitrile and diethylether were dried and degassed using the VAC 103991 solvent system and stored over 3-Å molecular sieves under a nitrogen atmosphere. Water was deionized with the Millipore Milli-Q UF Plus system.

The precursor [(PY5Me$_2$)MoI]I$_2$ was first synthesized. Solid PY5Me$_2$ (200 mg, 0.45 mmol) was added to a 20-mL toluene solution of MoI$_2$(CO)$_3$(MeCN)$_2$ (350 mg, 0.67 mmol) and the mixture was heated at reflux for 3 days. The solution was then cooled to room temperature and filtered to afford an orange solid, which was washed repeatedly with toluene until the filtrate was colorless. The solid was then extracted into 50 mL of acetonitrile, layered with 30 mL of diethylether, and allowed to stand for 2 days to yield orange rod-shaped crystals. The crystals were washed with 20 mL of diethylether to give a combined yield of 360 mg (87% with respect to PY5Me$_2$).

[(PY5Me$_2$)MoO]I$_2$: Solid [(PY5Me$_2$)MoI]I$_2$ (620 mg, 0.67 mmol) was added to 40 mL of deionized water and stirred in air for one day to give a green suspension. The water was then removed under reduced pressure and the green solid was washed with cold (0° C.) acetonitrile until the color of the filtrate changed from brown to green. The solid was then washed with 20 mL of diethylether to yield 470 mg (85%) of product.

[(PY5Me$_2$)MoO](PF$_6$)$_2$: A 20-mL acetonitrile solution of TI(PF$_6$) (401 mg, 1.15 mmol) was added drop wise to a stirred 20-mL acetonitrile solution of [(PY5Me$_2$)MoO]I$_2$ (465 mg, 0.575 mmol), and the mixture was stirred in air for 12 h. The solution was cooled to 0° C. and filtered to remove the yellow thallium iodide, and the bright green filtrate was concentrated to a volume of 20 mL under reduced pressure. Diffusion of diethylether vapor into this solution over the course of 3 days afforded 484 mg (95.0%) of product as green rod-shaped crystals.

Electrochemical studies employed a mercury pool working electrode with a surface area of 19.6 cm², which was stirred constantly during the CPE experiments. Electrical contact to the mercury pool was achieved through a platinum wire that remained immersed below the surface of the mercury, thereby avoiding contact with the solution, A 20.5 cm² platinum gauze (52 mesh, woven from 0.1 mm diameter wire) was utilized as the auxiliary electrode and was separated from the solution in the working electrode compartment by a medium-porosity sintered-glass frit. The reference electrode was a commercially available aqueous Ag/AgCl electrode, which was positioned within 5 mm of the working electrode, and the potentials are reported with respect to SHE by adding 0.195 V to the experimentally obtained values. The working electrode compartment contained 5-100 mL of electrolyte solution which was thoroughly sparged and kept under a blanket of water-saturated nitrogen during the experiments. A 0.6 M pH 7 phosphate buffer was used as electrolyte. Extended electrolyses of greater than 1 h were conducted in a larger cell containing 170 mL of 3 M pH 7 phosphate buffer in each compartment. The solutions in both compartments were vigorously stirred during the electrolysis. Sea water was obtained from Ocean Beach, San Francisco, and was passed through a course paper fitter prior to use in order to remove any particulate matter, iR compensation was employed for all experiments to account for the voltage drop between the reference and working electrodes using the BAS CV-50W software.

A mercury electrode was used in this study to reduce background activity of direct water reduction at the electrode at the high overpotentials needed to evaluate the catalyst. For catalysts which require lower overpotentials, other electrodes such as graphite and steel may be used.

It is to be noted that the turnover numbers and turnover frequencies reported in the text and figures of this application were generated prior to the filing of the referenced Provisional application, and these initial results were published thereafter (H. I. Karunadasa, C. J. Chang, J. R. Long, *Nature* 464, 1329 (2010)). At the time, it was assumed that all the metal-oxo catalyst molecules in solution contributed toward hydrogen generation. It was subsequently determined that only the metal-oxo catalyst molecules adsorbed on the surface of the mercury electrode of the experiments were catalytically active. Using cyclic voltammetry, the surface coverage of the catalyst molecules on the electrode was calculated to be ca. $10^{-10}$ mols/cm² (according to methods detailed in A. J. Bard, L. R. Faulkner, *Electrochemical Methods*, Wiley, New York, 1980). By following this approach, we were able to derive a more accurate estimate of the rates of hydrogen production, which are about 2 orders of magnitude greater than that earlier reported, and published. For example, in the extended electrolysis the turnover frequency was first reported as 8510 mols $H_2$/mol catalyst per h, when in fact (applying the new calculus) it was actually about 1,500,000 mol $H_2$/mol catalyst per h. Similarly, the reported turnover number of 606,000 mol $H_2$/mol catalyst is more accurately about 105,000,000 mol $H_2$/mol catalyst. These higher rates are comparable to those of hydrogenase enzymes on a per molecule basis, while packing together the number of catalyst molecules needed to fill the volume of a single hydrogenase protein yields hydrogen production rates of 200,000-600,000 $H_2$ molecules.

The discovery of a molecular molybdenum-oxo catalyst for generating hydrogen from water without use of additional acids and/or organic co-solvents establishes a new chemical paradigm for creating reduction catalysts that are highly active and robust in aqueous media. Importantly, the system employs an inexpensive, earth-abundant metal to achieve catalytic $H_2$ evolution from neutral buffered water or even seawater, maintaining long-term activity with TOF and TON values of 1.5 million mol $H_2$/mol catalyst per hour and 105 million mol $H_2$/mol catalyst, respectively. An overpotential of between 0.6 V to 1.0 V at the cathode leads to an efficiency of 67%-55% respectively for the cell, assuming that the rest of the cell operates at ideal efficiencies. The total voltage necessary for the cell depends on the reaction at the anode and well as the internal resistance of the cell which depends heavily on cell design, which does not constitute a part of this invention.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. An organo metal-oxo complex containing composition of matter comprising:
   $[(PY5W_2)MO]^{2+}$ wherein:
   $PY5W_2$ equals $(NC_5XYZ)(NC_5H_4)_4C_2W_2$;
   M equals Mo; and,
   W is methyl, X, Y, and Z are selected from the group comprising H, R, a halide, $CF_3$, or $SiR_3$, where R is an alkyl or aryl group.

2. The organo metal-oxo complex of claim 1 wherein the accompanying counter anion is $PF_6^-$.

* * * * *